(12) United States Patent (10) Patent No.: US 8,547,535 B2
Tezuka et al. (45) Date of Patent: Oct. 1, 2013

(54) COMPONENT MEASUREMENT APPARATUS

(75) Inventors: Shin-ichiro Tezuka, Musashino (JP); Hitoshi Hara, Musashino (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 185 days.

(21) Appl. No.: 13/040,872

(22) Filed: Mar. 4, 2011

(65) Prior Publication Data

US 2011/0216308 A1 Sep. 8, 2011

(30) Foreign Application Priority Data

Mar. 4, 2010 (JP) ................................. 2010-047716

(51) Int. Cl.
*G01N 33/48* (2006.01)
*G02B 7/04* (2006.01)

(52) U.S. Cl.
USPC ...................... 356/39; 250/201.3; 250/227.26

(58) Field of Classification Search
USPC ............................ 356/39; 250/201.3, 227.26
See application file for complete search history.

(56) References Cited

U.S. PATENT DOCUMENTS 3,013,467 A * 12/1961 Minsky ......................... 356/432
5,132,526 A * 7/1992 Iwasaki ....................... 250/201.3
6,548,796 B1 * 4/2003 Silvermintz et al. ........ 250/201.3

FOREIGN PATENT DOCUMENTS

| JP | 7-020048 A | 1/1995 |
|---|---|---|
| JP | 10-085976 A | 4/1998 |
| JP | 2000-225109 A | 8/2000 |
| JP | 2000-356510 A | 12/2000 |
| JP | 2004-102032 A | 4/2004 |
| JP | 2004-191114 A | 7/2004 |
| JP | 2005-028005 A | 2/2005 |
| JP | 2008-301944 A | 12/2008 |

OTHER PUBLICATIONS

Japanese Office Action dated Jan. 24, 2012, issued in corresponding Japanese Patent Application No. 2010-047716. (w/partial English translation).
Miyauchi, Y. et al. "Development of Noninvasive Blood Glucose Measuring Instrument by Near-Infrared Confocal Optical System," 8th Symposium of the Japanese Society for Medical and Biological Engineering, Apr. 23, 2009, pp. 7-8.
Miyauchi, Y. et al. "Noninvasive measurement of blood glucose level with use of near-infrared confocal laser," 48th Meeting of the Japan Society for Medical and Biological Engineers, Apr. 2009, p. 148.
Miyauchi, Y. et al. "Non- invasive method for measuring blood sugar level by confocal optical system with near-infrared laser" Symposium of Medicine and Biology 2009, Sep. 2009, p. 387.
Miyauchi, Y. et al. "Basis Examination for Development of Noninvasive Blood Glucose Measuring Instrument by Near-Infrared Confocal Optical System,", Aug. 2010.

* cited by examiner

*Primary Examiner* — Layla Lauchman
(74) *Attorney, Agent, or Firm* — Westerman, Hattori, Daniels & Adrian, LLP (57) ABSTRACT

A component measurement apparatus includes a laser that emits non-collimated laser light, an objective lens that condenses the non-collimated laser light emitted from the laser in order for the laser light to illuminate internal tissue of an object of measurement without collimating the laser light, a half mirror that redirects reflected light reflected by the internal tissue of the object of measurement and refracted by the objective lens, a pin hole through which the reflected light redirected by the half mirror passes, a light-receiving element that receives the reflected light having passed through a pin hole, and a data analyzer section that measures a component of the object of measurement in accordance with data output from the light-receiving element.

13 Claims, 10 Drawing Sheets

COMPONENT MEASUREMENT APPARATUS

BACKGROUND OF THE INVENTION

1. Field of the Invention

The present disclosure relates to component measurement apparatuses. A particular aspect of the present disclosure relates to improvement of a component measurement apparatus that measures concentrations and so forth of components using laser light.

2. Description of the Related Art

To date, in order to measure a concentration of a component such as a blood glucose level, in many cases human blood is collected with a syringe or by pricking a finger tip or an earlobe in order to measure a blood glucose concentration or so forth.

In general, a blood glucose level significantly changes depending on measurement conditions such as whether a subject has recently had a meal or not, or whether a subject performs exercise or not just before the blood sample is collected. Thus, frequent measurement is required in order to obtain correct blood glucose data. However, with a related art method in which a direct analysis is performed on a human blood sample that is collected every time such an analysis is performed, there is a problem in that the subject experiences a significant physical pain.

The assignee previously filed a patent application for a living body component measurement apparatus using a confocal optical system (see Japanese Unexamined Patent Application Publication No. 2008-301944). With this apparatus, a living body is illuminated by laser light, and the reflected light from the living body is detected. In accordance with a degree of laser light absorption by the living body (absorbance), the apparatus measures a concentration or so forth of a target component (for example, glucose in blood) without an invasive procedure for collecting a blood sample performed in the related art method.

Figure 10:
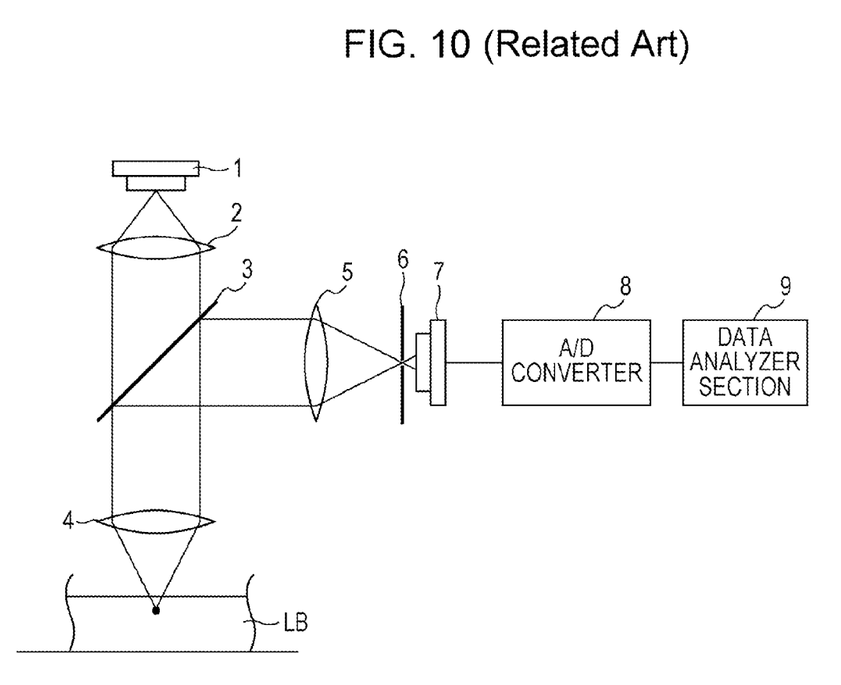
FIG. 10 is a block diagram illustrating an example of a related art living body component measurement apparatus.

FIG. 10 is a block diagram illustrating the living body component measurement apparatus disclosed in the above document. In FIG. 10, laser light emitted from a laser diode 1 is shaped into collimated light by a collimating lens 2 and strikes a half mirror 3 that is disposed so as to be inclined at about 45 degrees relative to the optical axis of the collimating lens 2. The laser diode 1 used here is, for example, a variable wavelength laser that can emit laser light in a wavelength region of 1600 nm to 1700 nm. Glucose absorbs a comparatively large amount of light in that wavelength region.

The collimated light having been transmitted through the half mirror 3 is condensed by an objective lens 4 and illuminates internal tissue of the living body LB. The laser light reflected by the internal tissue of the living body LB again strikes the objective lens 4, is shaped into collimated right, strikes the half mirror 3, and is redirected so as to be reflected at an angle of about 90 degrees.

The laser light, which has been reflected and redirected by the half mirror 3, is condensed by a lens 5 and strikes a pin hole 6. The laser light having passed through the pin hole 6 strikes a light-receiving element 7 and is converted into an electrical signal.

The light-receiving element 7 converts the received laser light into an electrical signal, the strength and the magnitude of which increase or decrease in accordance with the light amount of the received laser light, and sends the resultant signal to an analog to digital (A/D) converter 8. The A/D converter 8 converts the electrical signal received from the light-receiving element 7 into digital data, and sends the digital data to a data analyzer section 9.

When the living body LB is illuminated with laser light beams having two or more wavelengths different from each other, the data analyzer section 9 performs a quantitative analysis of a component of the living body LB in accordance with a plurality of electrical signals having been converted by and output from the light-receiving element 7.

Specifically, in order to quantitatively determine a blood glucose level, that is, a concentration of glucose in blood, a calibration curve that relates glucose concentrations having been measured to laser light absorbance values has been memorized in the data analyzer section 9 in advance. The data analyzer section 9 quantitatively determines a concentration of blood glucose of the living body LB in accordance with the calibration curve.

However, in the above-described related art living body component measurement apparatus, laser light emitted from the laser diode 1 is shaped into collimated light by the collimating lens 2 before the light strikes a half mirror 3. The laser light having been transmitted through the half mirror 3 is condensed by an objective lens 4 and illuminates internal tissue of the living body LB. As a result, there is a problem in that the living body component measurement apparatus needs considerable work time for assembly and adjustment such as alignment of the optical axes among optical components.

SUMMARY OF THE INVENTION

An object of the present disclosure is to achieve a component measurement apparatus, in which assembly and adjustment are comparatively easy, and with which measurement data from a desired measurement position in the object of measurement can be adequately obtained.

To achieve such a task, a component measurement apparatus according to an aspect of the present disclosure includes a laser that emits laser light, an objective lens that condenses the laser light emitted from the laser in order for the laser light to illuminate internal tissue of an object of measurement without shaping the laser light into collimated light, a half mirror that redirects reflected light reflected by the internal tissue of the object of measurement and refracted by the objective lens, a light-receiving element that receives the reflected light having passed through a pin hole through which the reflected light redirected by the half mirror passes, and a data analyzer section that measures a component of the object of measurement in accordance with data output from the light-receiving element.

Preferably, the laser is a variable wavelength light source in the component measurement apparatus.

Preferably, the laser, the objective lens, the pin hole, and the light-receiving element form a confocal optical system in the component measurement apparatus.

Preferably, a motion drive mechanism that moves the confocal optical system and the object of measurement relatively to each other in three dimensions is included in the component measurement apparatus.

Preferably, the component of the object of measurement is glucose in blood, and the data analyzer section quantitatively determines a concentration of the glucose by measuring absorbance of the glucose in the internal tissue of the object of measurement in accordance with the data output from the light-receiving element and determines a blood glucose level in the component measurement apparatus.

Preferably, the component measurement apparatus includes a unit for causing a beam of the laser light emitted from the laser to diverge.

Preferably, the component measurement apparatus further includes an optical fiber used to illuminate a surface of the object of measurement with the output light of the laser, a second light-receiving element that detects the reflected light reflected by the surface of the object of measurement due to illumination using the optical fiber, and a laser driver circuit that drives the laser so as to maintain the output light intensity of the laser at a certain value in accordance with a detection signal of the second light-receiving element.

Preferably, the data analyzer section measures the component of the object of measurement in accordance with normalized data obtained by dividing a detection signal of the light-receiving element that receives the reflected light having passed through the pin hole by the detection signal of the second light-receiving element in the component measurement apparatus. The data analyzer can be a computer, or it can be a logic-containing circuit board or the like.

Preferably, the laser includes a third light-receiving element therein that monitors the output light thereof, and the laser driver circuit drives the laser in accordance with at least one of the detection signal of the second light-receiving element and a detection signal of the third light-receiving element so as to maintain the output light intensity of the laser at a certain value in the component measurement apparatus.

Preferably, the laser includes a third light-receiving element therein that monitors the output light thereof, and the data analyzer section measures the component of the object of measurement in accordance with normalized data obtained by dividing a detection signal of the light-receiving element that receives the reflected light having passed through the pin hole by at least one of the detection signal of the second light-receiving element and a detection signal of the third light-receiving element in the component measurement apparatus.

Preferably, the laser includes a third light-receiving element therein that monitors the output light thereof, and the data analyzer section measures the component of the object of measurement in accordance with data obtained by linear combination of a first normalized signal and a second normalized signal. The first normalized signal is obtained by dividing a detection signal of the light-receiving element that receives the reflected light having passed through the pin hole by the detection signal of the second light-receiving element. The second normalized signal is obtained by dividing the detection signal of the light-receiving element that receives the reflected light having passed through the pin hole by a detection signal of the third light-receiving element in the component measurement apparatus.

Preferably, the component measurement apparatus includes a fourth light-receiving element that detects the reflected light reflected by the half mirror, and the laser driver circuit drives the laser in accordance with at least one of the detection signal of the second light-receiving element, the detection signal of the third light-receiving element, and a detection signal of the fourth light-receiving element so as to maintain the output light intensity of the laser at a certain value.

Preferably, the data analyzer section measures the component of the object of measurement in accordance with normalized data obtained by dividing the detection signal of the light-receiving element that receives the reflected light having passed through the pin hole by at least one of the detection signal of the second light-receiving element, the detection signal of the third light-receiving element, and the detection signal of the fourth light-receiving element in the component measurement apparatus.

Preferably, the data analyzer section measures the component of the object of measurement in accordance with data obtained by linear combination of normalized signals obtained by dividing the detection signal of the light-receiving element that receives the reflected light having passed through the pin hole by each of the detection signals of the second, third, and fourth light-receiving elements in the component measurement apparatus.

With the structure described as above, the component measurement apparatus that can be comparatively easily assembled and adjusted is achieved, and with this component measurement apparatus, measurement data for a desired position in an object of measurement can be adequately obtained.

DESCRIPTION OF THE PREFERRED EMBODIMENTS

Figure 1:
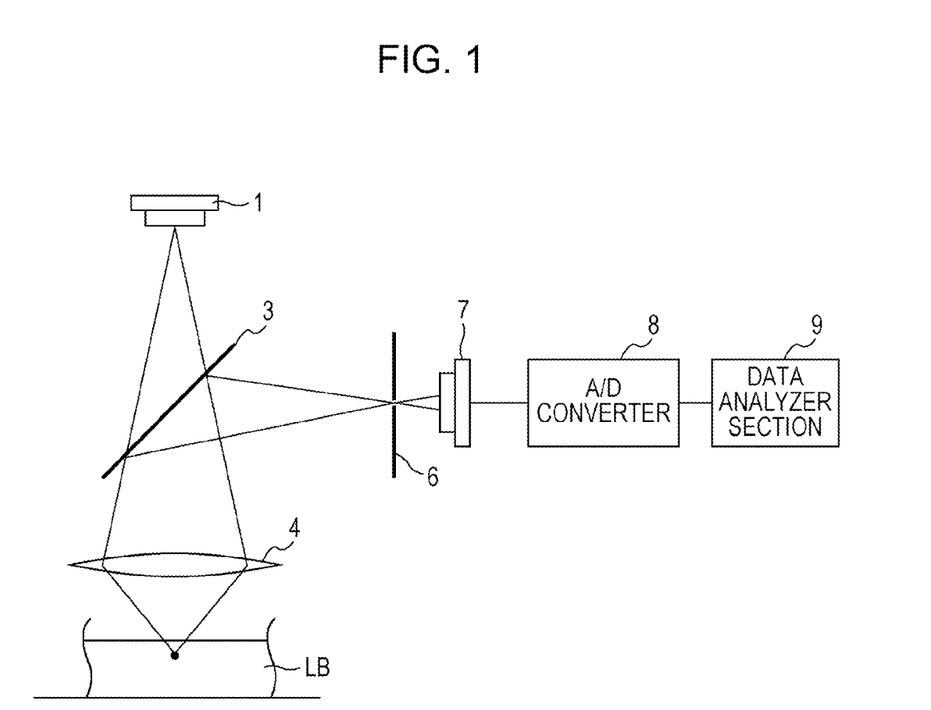
FIG. 1 is a block diagram illustrating an embodiment according to the present disclosure.

Embodiments according to the present disclosure will be described below in detail with reference to the drawings. FIG. 1 is a block diagram illustrating an embodiment according to the present disclosure. Components similar to those in FIG. 10 are denoted by similar signs. A difference between an apparatus illustrated in FIG. 1 and the apparatus illustrated in FIG. 10 is that the apparatus illustrated in FIG. 1 illuminates internal tissue of a living body as an object of measurement with laser output light having been condensed by an objective lens without being shaped into collimated light.

Referring to FIG. 1, the laser light emitted from a laser diode 1 strikes a half mirror 3 that is disposed so as to be inclined at about 45 degrees relative to the optical axis of the laser diode 1. The laser diode 1 used here is, for example, a variable wavelength laser that can emit laser light in a wavelength region of 1500 nm to 1700 nm. Glucose absorbs a comparatively large amount of light in that wavelength region. When one laser diode cannot emit laser light in the 1500 nm to 1700 nm wavelength region, a combination of a plurality of laser diodes can be used. Laser light having been transmitted through the half mirror 3 is condensed by an objective lens 4 and illuminates the internal tissue of the living body LB. The laser diode 1, the half mirror 3, and the objective lens 4 are included in an illumination system that illuminates the internal tissue of the living body LB. The illumination system is disposed so as to make the optical axis thereof oppose the living body LB.

The laser light reflected by the internal tissue of the living body LB again strikes the half mirror 3 through the objective lens 4, and is redirected so as to be reflected at an angle of about 90 degrees. The laser light, which has been reflected and redirected by the half mirror 3, directly strikes a pin hole 6 without passing through a lens. The laser light having passed through the pin hole 6 strikes a light-receiving element 7 and is converted into an electrical signal.

The light-receiving element 7 converts the received laser light into an electrical signal, the strength and the magnitude of which increase or decrease in accordance with the light amount of the received laser light, and sends the resultant signal to an analog to digital (A/D) converter 8. The A/D converter 8 converts the electrical signal received from the light-receiving element 7 into digital data, and sends the digital data to a data analyzer section 9. The pin hole 6 and the light-receiving element 7 are included in a light receiver system, which is arranged such that the optical axis thereof extends in a direction perpendicular to the optical axis of the illumination system. In addition, the laser diode 1, the objective lens 4, the pin hole 6, and the light-receiving element 7 form a confocal optical system.

When the living body LB is illuminated with laser light beams having two or more wavelengths different from each other, the data analyzer section 9 performs a quantitative analysis of a component of the living body LB in accordance with a plurality of electrical signals having been converted by and output from the light-receiving element 7.

With such a structure, the lenses 2 and 5 illustrated in FIG. 10 are not required. Thus, compared to the apparatus illustrated in FIG. 10, assembly and adjustment such as alignment of the optical axes among optical components can be simplified.

In addition, a measurement position in the living body LB is illuminated with laser light emitted from the laser diode 1. The laser light is condensed by the objective lens 4 without being shaped into collimated light. Thus, measurement data from a desired measurement position in the living body LB can be adequately obtained.

Figure 2:
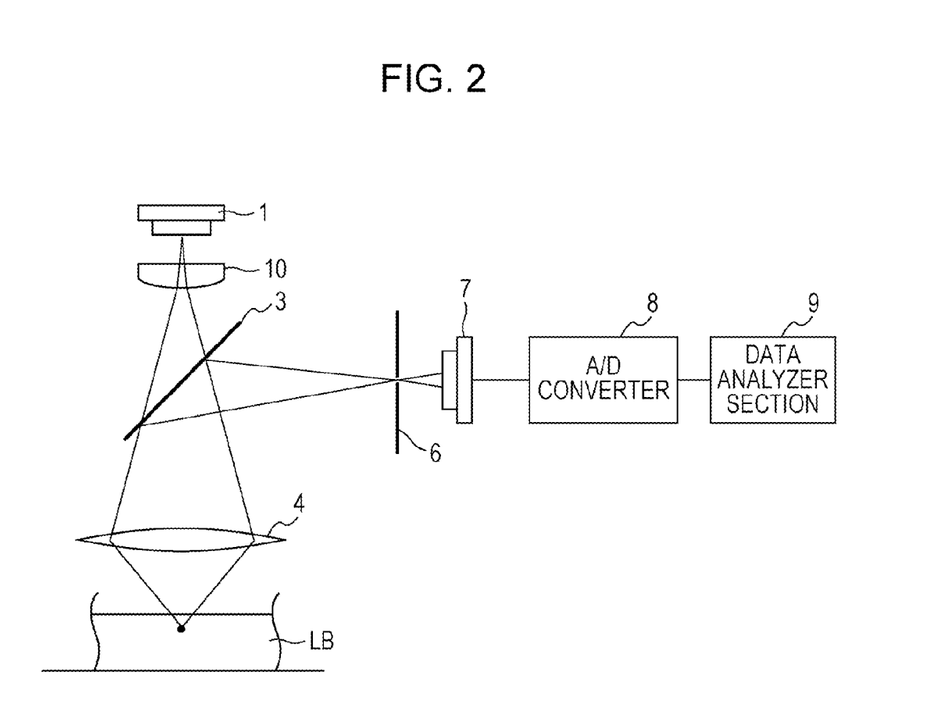
FIG. 2 is a block diagram illustrating another embodiment according to the present disclosure.

FIG. 2 is a block diagram illustrating another embodiment according to the present disclosure. In the embodiment illustrated in FIG. 2, a plano-convex lens 10 causes a beam of laser light emitted from the laser diode 1 to diverge. By doing this, the optical path length can be decreased compared to that illustrated in FIG. 1 and the size of the apparatus can be reduced corresponding to the decreased optical path length.

Figure 3:
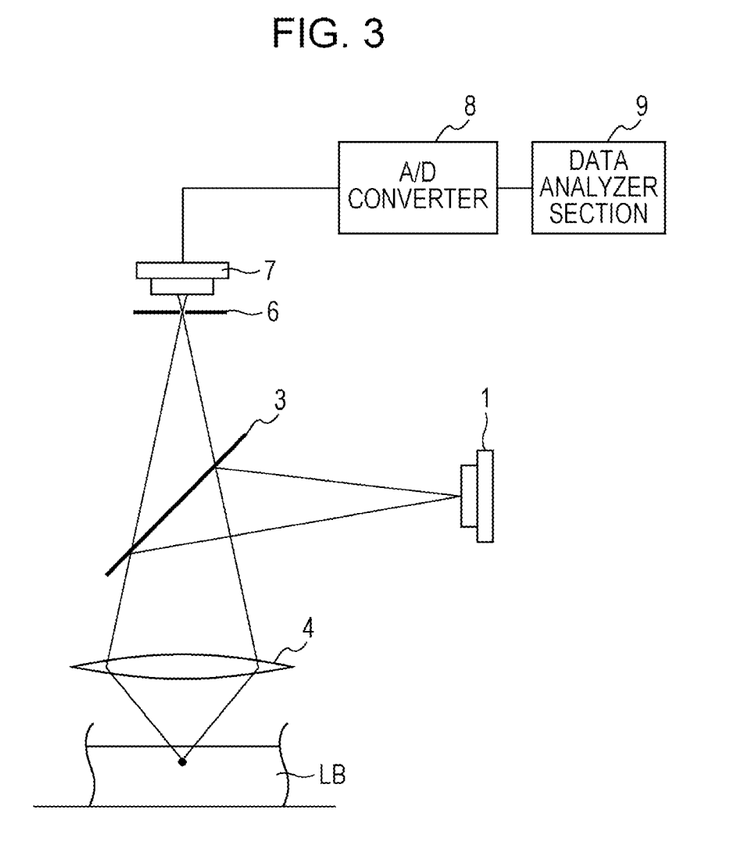
FIG. 3 is a block diagram illustrating yet another embodiment according to the present disclosure.

FIG. 3 is a block diagram illustrating yet another embodiment according to the present disclosure. In the embodiment illustrated in FIG. 3, the light receiver system including the pin hole 6 and the light-receiving element 7 is disposed so as to oppose the living body LB, and the laser diode 1 is disposed in a direction perpendicular to the optical axis of the light receiver system. By doing this, component measurement similar to that performed with the apparatus in FIG. 1 can be performed.

Also with the structure in FIG. 3, by disposing the plano-convex lenses 10 each similar to the plano-convex lens 10 illustrated in FIG. 2 in front of the laser diode 1 and between the pin hole 6 on the light-receiving element 7 side and the half mirror 3, a beam of laser light can diverge and the optical path length can be decreased. Thus, the size of the apparatus can be reduced.

Figure 4:
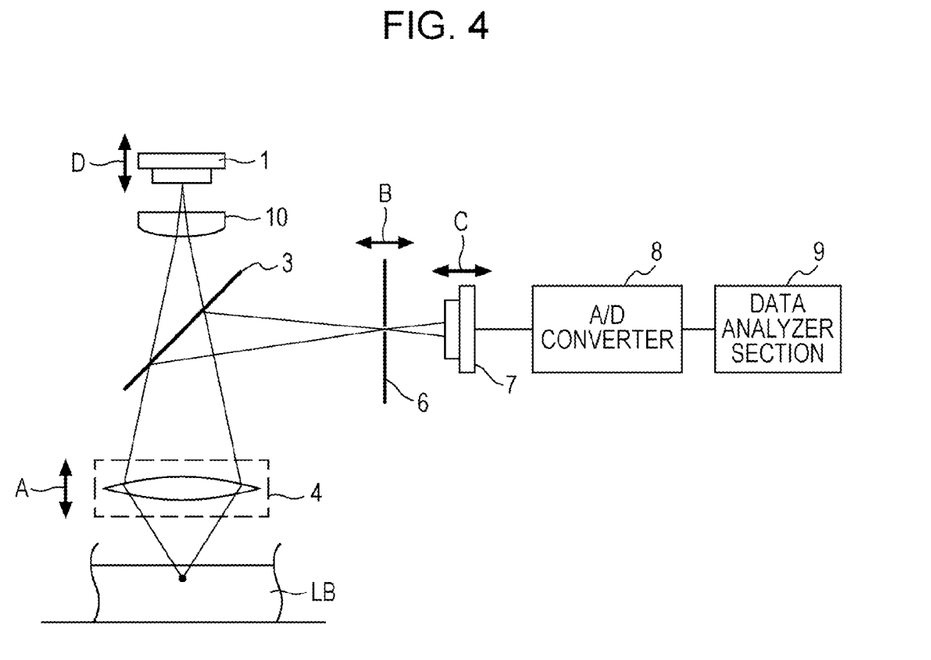
FIG. 4 is a block diagram illustrating yet another embodiment according to the present disclosure.

FIG. 4 is a block diagram illustrating yet another embodiment according to the present disclosure. In the embodiment illustrated in FIG. 4, the objective lens 4 is movably arranged along the direction of an optical axis A. By doing this, an imaging position in the living body LB can be moved in a depth direction.

An alternative structure may be possible, in which the pin hole 6 moves along a direction of an optical axis B and the light-receiving element 7 moves along a direction of an optical axis C in accordance with the movement of the objective lens 4.

Also in the structure illustrated in FIG. 4, by incorporating a mechanism that moves a component measurement apparatus including the illumination and the light receiver systems and the living body LB relatively to each other in the X and Y directions, three-dimensional information in the living body LB can be obtained.

In the embodiment illustrated in FIG. 4, the objective lens 4 is movably arranged along the direction of the optical axis A. It is also possible that the objective lens 4 is fixed and the laser diode 1 is set to be movable along a direction of an optical axis D, and the pin hole 6 and the light-receiving element 7 are set to respectively move in the directions of the optical axes B and C in synchronization with the movement of the laser diode 1.

Figure 5:
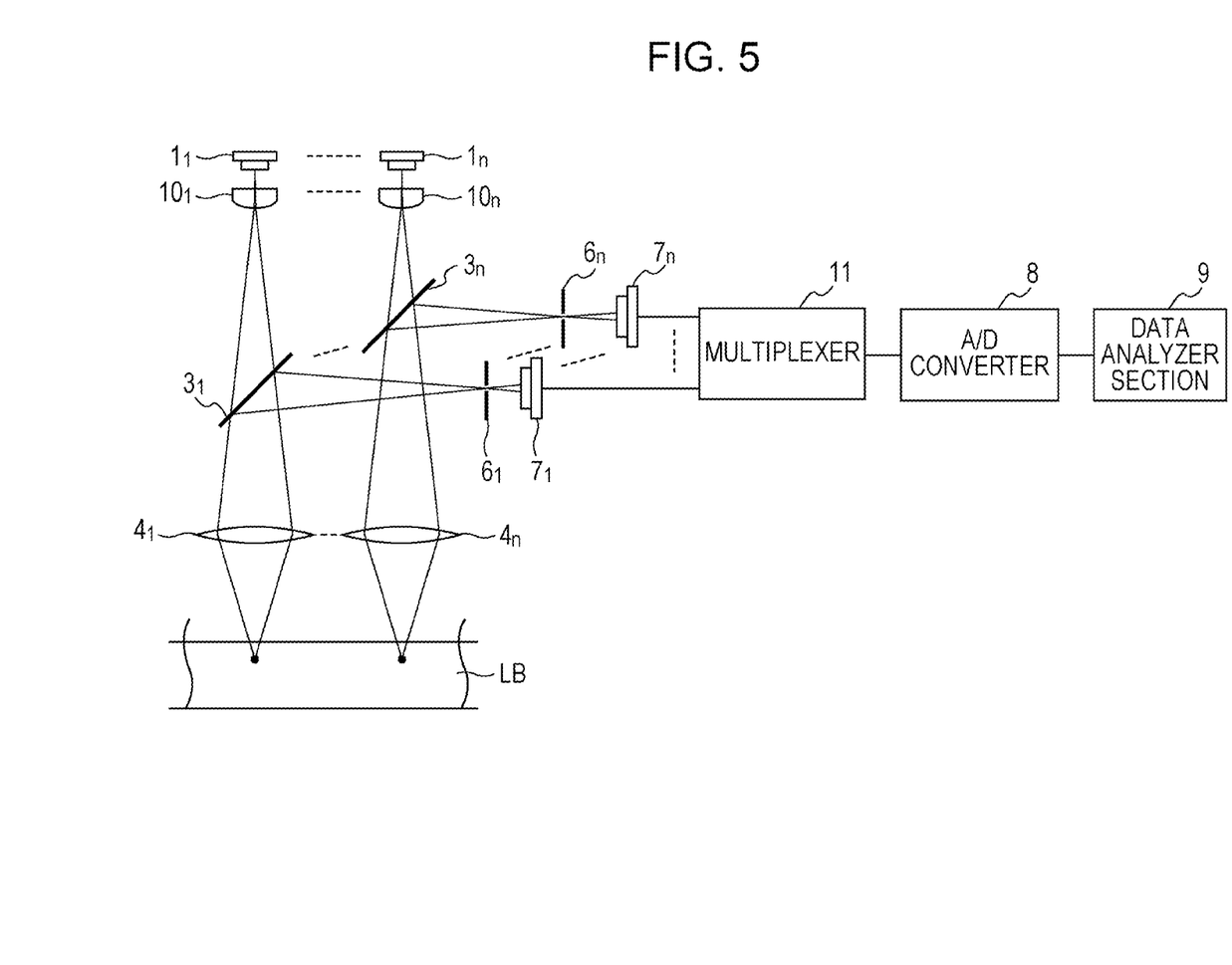
FIG. 5 is a block diagram illustrating yet another embodiment according to the present disclosure.

FIG. 5 is a block diagram illustrating yet another embodiment according to the present disclosure. In the embodiment illustrated in FIG. 5, the component measurement apparatus structured as illustrated in FIG. 2 is unitized, and a plurality of such units, that is, n units, are integrated in an array. By arranging those measurement units into the array, signals of different focal positions in the living body LB and of different wavelengths can be collectively obtained. Output signals from the individual light-receiving elements 7 are sent to the common A/D converter 8 through a multiplexer 11 and converted into digital data. However, when processing at higher speed is required, each light-receiving element can be provided with a dedicated A/D converter.

In each of the above-described embodiments, by driving the laser diode 1 by an automatic output control loop so as to maintain the intensity of light emitted from the laser diode 1 toward the object of measurement at a certain value, stable measurement can be performed.

Figure 6:
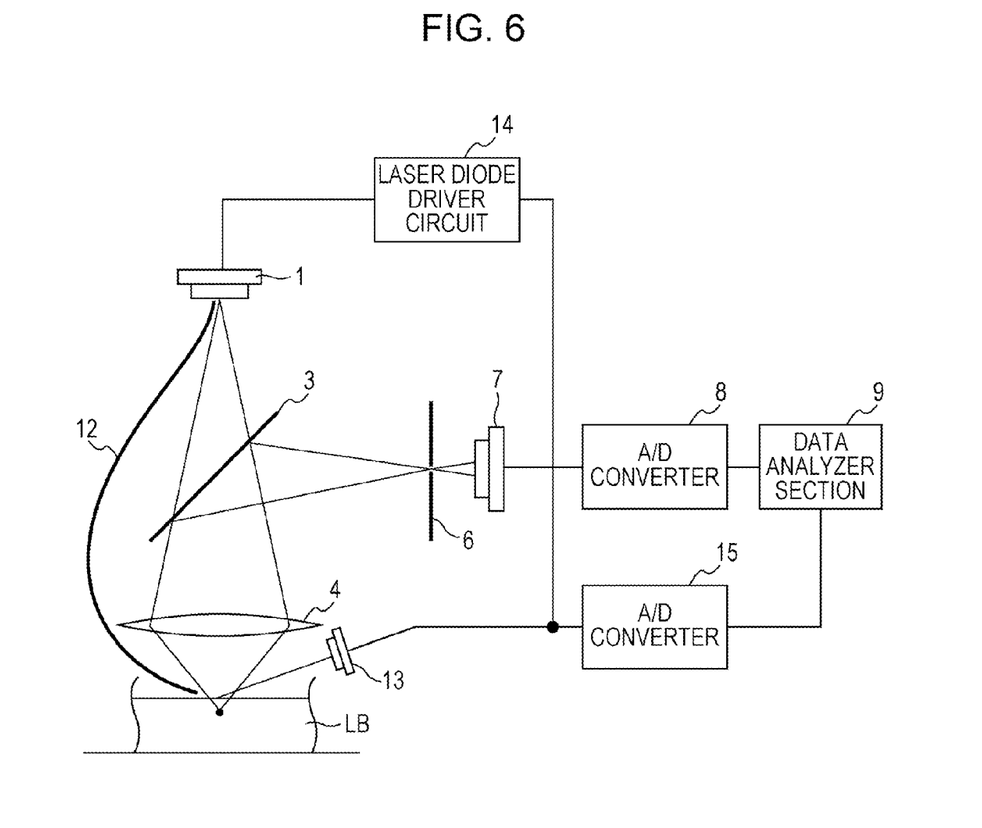
FIG. 6 is a block diagram illustrating yet another embodiment according to the present disclosure.

FIG. 6 is a block diagram illustrating an example in which the above-described structure is applied to the embodiment illustrated in FIG. 1. In the embodiment illustrated in FIG. 6, a surface of the living body LB as the object of measurement is illuminated with part of output light emitted from the laser diode 1 through an optical fiber 12. The light reflected by the surface of the living body LB is detected by a second light-receiving element 13. An output signal of this second light-receiving element 13 is sent to a laser diode driver circuit 14 in order to drive the laser diode 1 so as to maintain the output light intensity of the laser diode 1 at a certain value.

By doing this, changes in the output light intensity caused by temperature changes and spatial intensity variations of the laser diode 1 can be suppressed and a stable component measurement result can be obtained.

The output signal of the second light-receiving element 13 is also sent to the data analyzer section 9 through an A/D converter 15, and the output signal of the first light-receiving element 7 is divided by the output signal of the second light-receiving element 13 in order to be normalized. By doing this, output fluctuations of the laser diode 1 and variations due to reflection at the surface of the living body LB can be compensated for.

Figure 7:
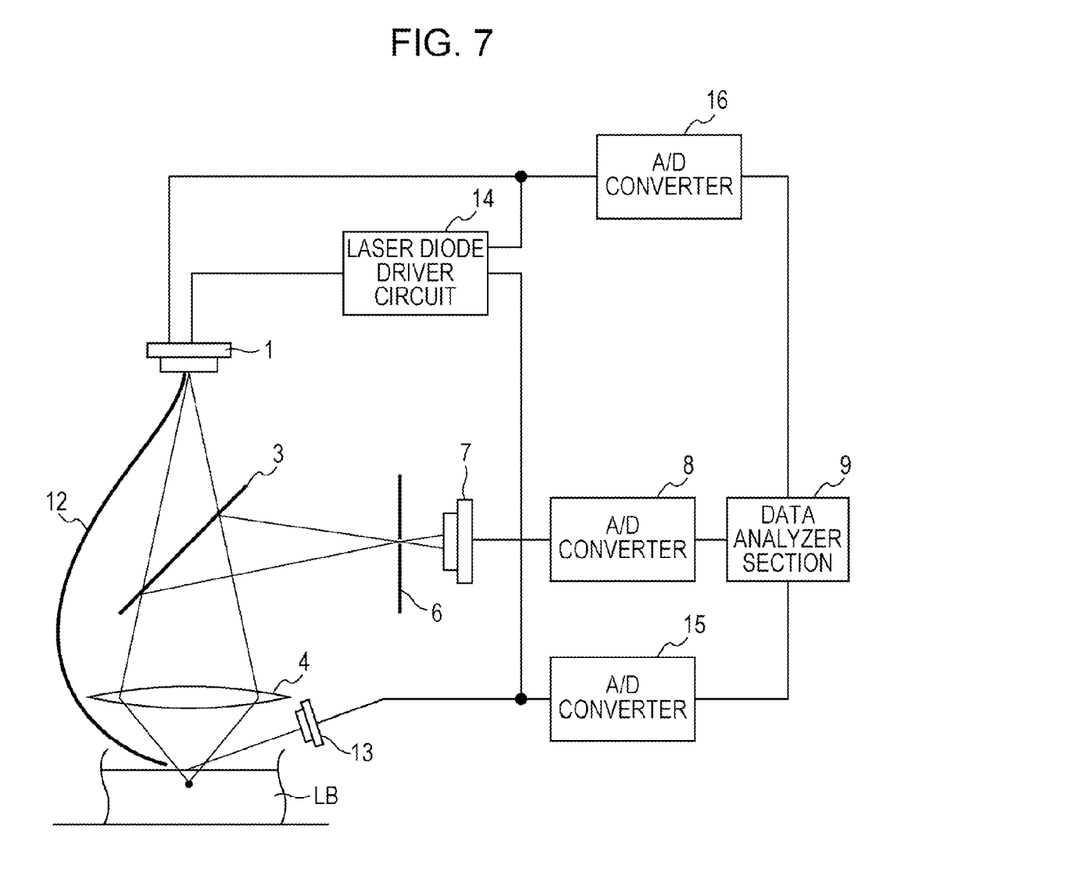
FIG. 7 is a block diagram illustrating yet another embodiment according to the present disclosure.

FIG. 7 is a block diagram illustrating an embodiment, in which the laser diode 1 illustrated in FIG. 6 includes a third light-receiving element (not shown) therein that monitors the output light thereof. An output signal of the third light-receiving element is also sent to the laser diode driver circuit 14 in order to drive the laser diode 1 so as to maintain the output light intensity of the laser diode 1 at a certain value.

The output signal of the third light-receiving element is also sent to the data analyzer section 9 through an A/D converter 16, and the output signal of the first light-receiving element 7 is divided by the output signal of the third light-receiving element in order to be normalized. By doing this, in the data analyzer section 9, the two normalized signals are linearly combined and a coupling factor is determined by a multivariate analysis. In accordance with these values, output fluctuations of the laser diode 1 and variations due to reflection at the surface of the living body LB are compensated for with a high degree of accuracy.

Figure 8:
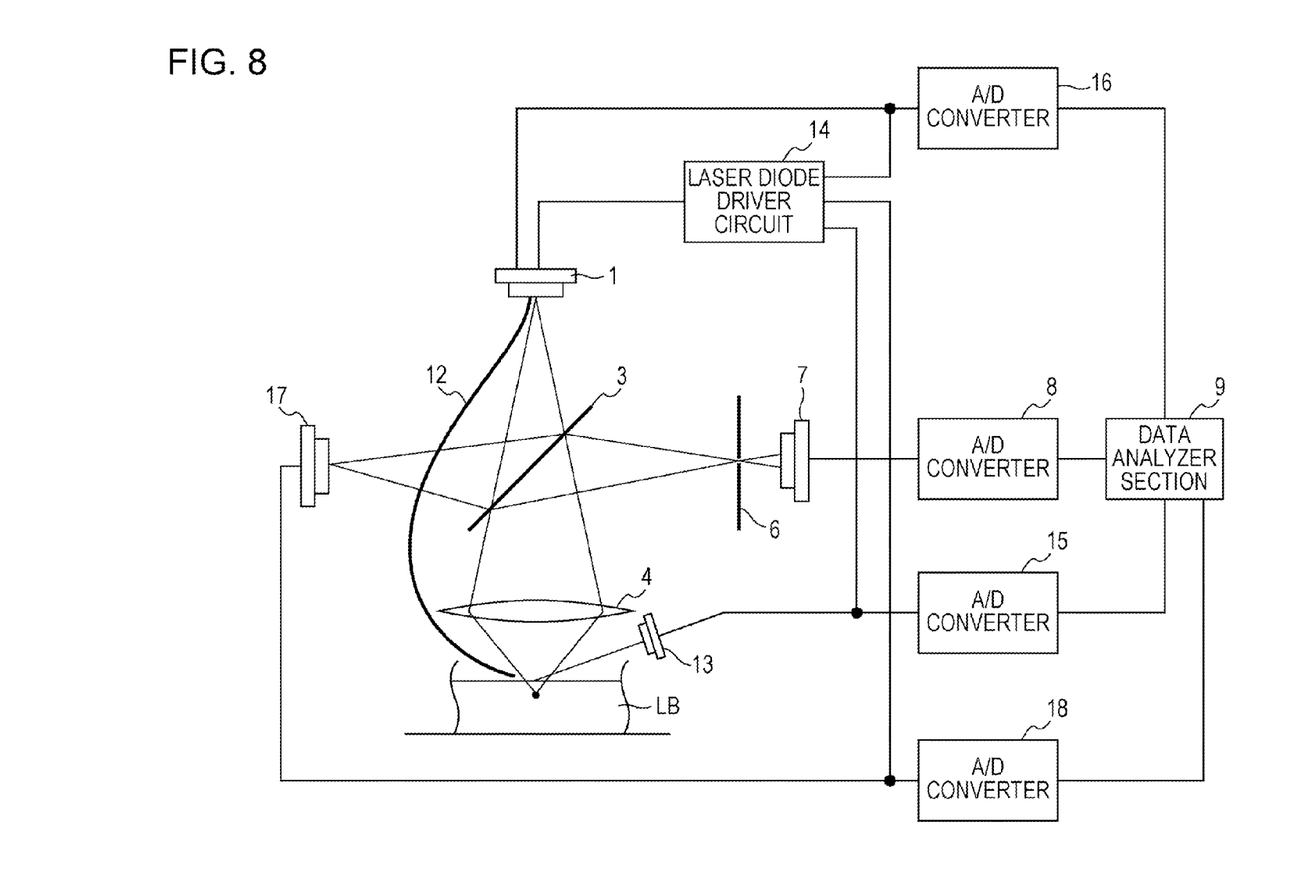
FIG. 8 is a block diagram illustrating yet another embodiment according to the present disclosure.

Referring to FIG. 8, a fourth light-receiving element 17, which detects the reflected light reflected by the half mirror 3, and an A/D converter 18, which converts an output signal of this fourth light-receiving element 17 into a digital signal, are further added to the embodiment illustrated in FIG. 7. The fourth light-receiving element 17 detects spatial variations of output light emitted from the laser diode 1. An output signal of the fourth light-receiving element 17 is also sent to the laser diode driver circuit 14 in order to drive the laser diode 1 so as to maintain the output light intensity of the laser diode 1 at a certain value.

The output signal of the fourth light-receiving element 17 is also sent to the data analyzer section 9 through the A/D converter 18, and the output signal of the first light-receiving element 7 is divided by the output signal of the fourth light-receiving element 17 in order to be normalized. By doing this, in the data analyzer section 9, the three normalized signals are linearly combined and a coupling factor is determined by a multivariate analysis. In accordance with these values, spatial variations and output fluctuations of the laser diode 1 and variations due to reflection at the surface of the living body LB are compensated for with a higher degree of accuracy.

Figure 9:
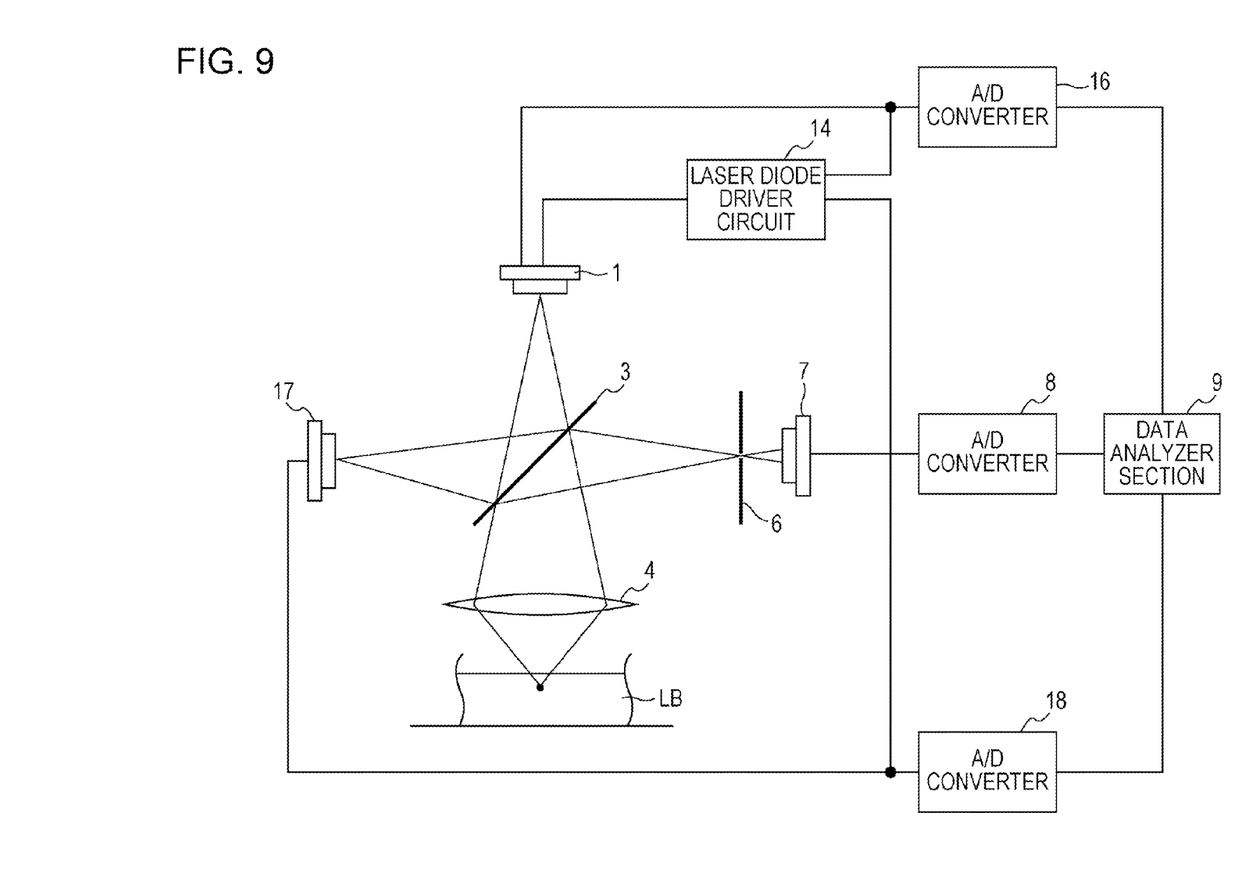
FIG. 9 is a block diagram illustrating yet another embodiment according to the present disclosure.

Referring to FIG. 9, a signal system including the optical fiber 12, the second light-receiving element 13, and the A/D converter 15 of the embodiment illustrated in FIG. 8 has been omitted. According to a structure illustrated in FIG. 9, the laser diode driver circuit 14 drives the laser diode 1 in accordance with the output signals of the third light-receiving element and the fourth light-receiving element 17 so as to maintain the output light intensity of the laser diode 1 at a certain value. With the data analyzer section 9, output fluctuations and spatial variations of the laser diode 1 can be compensated for with a high degree of accuracy in accordance with a normalized signal obtained by dividing the output signal of the first light-receiving element 7 by the output signal of the third light-receiving element and another normalized signal obtained by dividing the output signal of the first light-receiving element 7 by the output signal of the fourth light-receiving element 17.

The laser diode 1 used in each of the embodiments illustrated in FIGS. 8 and 9 includes the third light-receiving element therein that monitors the output light thereof. However, the laser diode 1 that does not include the third light-receiving element as illustrated in FIG. 6 may be used depending on compensation accuracy required by the apparatus.

The structures illustrated in FIGS. 6 to 9 may be applicable not only to the embodiment illustrated in FIG. 1, but also to the embodiments illustrated in FIGS. 2 to 5.

In each of the above-described embodiments, an example is described, in which a fixed focus lens is used as the objective lens 4. However, a varifocal lens may instead be used as the objective lens 4. As a varifocal lens, a liquid crystal lens may be used. The liquid crystal lens has a structure in which, for example, a space formed to have a lens-like shape is filled with liquid crystals encapsulated therein and the refractive index of the liquid crystals is in effect changed by adjusting an applied voltage. With the liquid crystal lens, the focal distance changes in accordance with changes in the refractive index of the material despite the shape of the lens being unchanged.

By the use of such a varifocal lens as the objective lens 4, a measurement position in the depth direction in the tissue of the living body LB can be desirably set by adjusting the voltage applied to the varifocal lens without moving the position of the objective lens 4 along the optical axis. Thus, the lens movement mechanism can be simplified.

In each of the above-described embodiments, an example is described, in which a variable wavelength laser is used as the light source. However, the light source may be a single wavelength laser when a target component is specified.

In each of the above-described embodiments, an example in which a blood glucose level in human blood is measured is described. However, the above-described examples are useful in quantitative measurement of a blood component and a tissue fluid component in addition to the measurement of a blood glucose level.

Also, an object of measurement is not limited to a human body. The apparatus is useful in quantitative measurement of an internal substance of an animal or a plant.

Furthermore, an object of measurement is not limited to a living body. The apparatus is also useful in non-destructive inspection of the structure and the composition of an agricultural product, a fishery product, food, an organic material, and so forth and in quantitative measurement of a chemical substance.

As described above, according to the present disclosure, the component measurement apparatus is achieved, of which assembly and adjustment are comparatively easy and with which measurement data for a desired position in an object of measurement can be adequately obtained. Thus, the component measurement apparatus is suitable for measurement of a variety of components such as a blood glucose level in human blood.

What is claimed is:

1. A component measurement apparatus comprising:
   a laser that emits non-collimated laser light;
   an objective lens that condenses the non-collimated laser light emitted from the laser in order for the laser light to illuminate internal tissue of an object of measurement without shaping the laser light into collimated light;
   a half mirror that redirects reflected light reflected by the internal tissue of the object of measurement and refracted by the objective lens;
   a pin hole through which the reflected light redirected by the half mirror passes;
   a first light-receiving element that receives the reflected light having passed through the pin hole;
   a data analyzer section that measures a component of the object of measurement in accordance with data output from the first light-receiving element;
   an optical fiber used to illuminate a surface of the object of measurement with the output light of the laser;
   a second light-receiving element that detects reflected light reflected by the surface of the object of measurement due to the illumination using the optical fiber; and
   a laser driver circuit that drives the laser so as to maintain an output light intensity of the laser at a certain value in accordance with a detection signal of the second light-receiving element.

2. The component measurement apparatus according to claim 1,
   wherein the data analyzer section measures the component of the object of measurement in accordance with normalized data obtained by dividing a detection signal of the first light-receiving element by the detection signal of the second light-receiving element.

3. The component measurement apparatus according to claim 1, wherein the laser includes a third light-receiving element therein that monitors the output light thereof, and
wherein the laser driver circuit drives the laser in accordance with at least one of the detection signal of the second light-receiving element and a detection signal of the third light-receiving element so as to maintain the output light intensity of the laser at a certain value.

4. The component measurement apparatus according to claim 1,
wherein the laser includes a third light-receiving element therein that monitors the output light thereof, and
wherein the data analyzer section measures the component of the object of measurement in accordance with normalized data obtained by dividing a detection signal of the first light-receiving element by at least one of the detection signal of the second light-receiving element and a detection signal of the third light-receiving element.

5. The component measurement apparatus according to claim 1,
wherein the laser includes a third light-receiving element therein that monitors the output light thereof, and
wherein the data analyzer section measures the component of the object of measurement in accordance with data obtained by linear combination of a first normalized signal and a second normalized signal, the first normalized signal being obtained by dividing a detection signal of the first light-receiving element by the detection signal of the second light-receiving element, the second normalized signal being obtained by dividing the detection signal of the first light-receiving element by a detection signal of the third light-receiving element.

6. The component measurement apparatus according to claim 3, further comprising:
a fourth light-receiving element that detects the reflected light reflected by the half mirror,
wherein the laser driver circuit drives the laser in accordance with at least one of the detection signal of the second light-receiving element, the detection signal of the third light-receiving element, and a detection signal of the fourth light-receiving element so as to maintain the output light intensity of the laser at a certain value.

7. The component measurement apparatus according to claim 6,
wherein the data analyzer section measures the component of the object of measurement in accordance with normalized data obtained by dividing the detection signal of the first light-receiving element by at least one of the detection signal of the second light-receiving element, the detection signal of the third light-receiving element, and the detection signal of the fourth light-receiving element.

8. The component measurement apparatus according to claim 6,
wherein the data analyzer section measures the component of the object of measurement in accordance with data obtained by linear combination of normalized signals obtained by dividing the detection signal of the first light-receiving element by each of the detection signals of the second, third, and fourth light-receiving elements.

9. A component measurement apparatus comprising:
a laser that is a variable wavelength light source emitting non-collimated laser light
an objective lens that condenses the non-collimated laser light emitted from the laser in order for the laser light to illuminate internal tissue of an object of measurement without shaping the laser light into collimated light;
a half mirror that redirects reflected light reflected by the internal tissue of the object of measurement and refracted by the objective lens;
a pin hole through which the reflected light redirected by the half mirror passes;
a first light-receiving element that receives the reflected light having passed through the pin hole;
a data analyzer section that measures a component of the object of measurement in accordance with data output from the first light-receiving element;
an optical fiber used to illuminate a surface of the object of measurement with the output light of the laser;
a second light-receiving element that detects reflected light reflected by the surface of the object of measurement due to the illumination using the optical fiber; and
a laser driver circuit that drives the laser so as to maintain an output light intensity of the laser at a certain value in accordance with a detection signal of the second light-receiving element.

10. A component measurement apparatus comprising:
a laser that emits non-collimated laser light;
an objective lens that condenses the non-collimated laser light emitted from the laser in order for the laser light to illuminate internal tissue of an object of measurement without shaping the laser light into collimated light;
a half mirror that redirects reflected light reflected by the internal tissue of the object of measurement and refracted by the objective lens;
a pin hole through which the reflected light redirected by the half mirror passes;
a first light-receiving element that receives the reflected light having passed through the pin hole, wherein the laser, the objective lens, the pin hole, and the first light-receiving element form a confocal optical system;
a data analyzer section that measures a component of the object of measurement in accordance with data output from the first light-receiving element;
an optical fiber used to illuminate a surface of the object of measurement with the output light of the laser;
a second light-receiving element that detects reflected light reflected by the surface of the object of measurement due to the illumination using the optical fiber; and
a laser driver circuit that drives the laser so as to maintain an output light intensity of the laser at a certain value in accordance with a detection signal of the second light-receiving element.

11. A component measurement apparatus comprising:
a laser that emits non-collimated laser light;
an objective lens that condenses the non-collimated laser light emitted from the laser in order for the laser light to illuminate internal tissue of an object of measurement without shaping the laser light into collimated light;
a half mirror that redirects reflected light reflected by the internal tissue of the object of measurement and refracted by the objective lens;
a pin hole through which the reflected light redirected by the half mirror passes;
a first light-receiving element that receives the reflected light having passed through the pin hole, wherein the laser, the objective lens, the pin hole, and the first light-receiving element form a confocal optical system;

a data analyzer section that measures a component of the object of measurement in accordance with data output from the first light-receiving element;

an optical fiber used to illuminate a surface of the object of measurement with the output light of the laser;

a second light-receiving element that detects reflected light reflected by the surface of the object of measurement due to the illumination using the optical fiber;

a laser driver circuit that drives the laser so as to maintain an output light intensity of the laser at a certain value in accordance with a detection signal of the second light-receiving element; and a motion drive mechanism that moves the confocal optical system and the object of measurement relatively to each other in three dimensions.

12. A component measurement apparatus comprising:

a laser that emits non-collimated laser light;

an objective lens that condenses the non-collimated laser light emitted from the laser in order for the laser light to illuminate internal tissue of an object of measurement without shaping the laser light into collimated light;

a half mirror that redirects reflected light reflected by the internal tissue of the object of measurement and refracted by the objective lens;

a pin hole through which the reflected light redirected by the half mirror passes;

a first light-receiving element that receives the reflected light having passed through the pin hole;

a data analyzer section that measures a component of the object of measurement in accordance with data output from the first light-receiving element;

an optical fiber used to illuminate a surface of the object of measurement with the output light of the laser;

a second light-receiving element that detects reflected light reflected by the surface of the object of measurement due to the illumination using the optical fiber; and a laser driver circuit that drives the laser so as to maintain an output light intensity of the laser at a certain value in accordance with a detection signal of the second light-receiving element, wherein the component of the object of measurement is glucose in blood, and wherein the data analyzer section quantitatively determines a concentration of the glucose by measuring absorbance of the glucose in the internal tissue of the object of measurement in accordance with the data output from the first light-receiving element and determines a blood glucose level.

13. A component measurement apparatus comprising:

a laser that emits non-collimated laser light;

an objective lens that condenses the non-collimated laser light emitted from the laser in order for the laser light to illuminate internal tissue of an object of measurement without shaping the laser light into collimated light;

a half mirror that redirects reflected light reflected by the internal tissue of the object of measurement and refracted by the objective lens;

a pin hole through which the reflected light redirected by the half mirror passes;

a first light-receiving element that receives the reflected light having passed through the pin hole;

a data analyzer section that measures a component of the object of measurement in accordance with data output from the first light-receiving element;

a lens for causing a beam of the laser light emitted from the laser to diverge;

an optical fiber used to illuminate a surface of the object of measurement with the output light of the laser;

a second light-receiving element that detects reflected light reflected by the surface of the object of measurement due to the illumination using the optical fiber; and a laser driver circuit that drives the laser so as to maintain an output light intensity of the laser at a certain value in accordance with a detection signal of the second light-receiving element.

* * * * *